United States Patent
Ichim et al.

(10) Patent No.: US 11,655,474 B2
(45) Date of Patent: May 23, 2023

(54) SUPPRESSION OF PATHOLOGICAL ANGIOGENESIS BY INHIBITION OF NR2F6

(71) Applicant: Regen Biopharma, Inc., Medina, MN (US)

(72) Inventors: Thomas Ichim, San Diego, CA (US); David Koos, La Mesa, CA (US)

(73) Assignee: Regen Biopharma, Inc., La Mesa, CA (US)

( * ) Notice: Subject to any disclaimer, the term of this patent is extended or adjusted under 35 U.S.C. 154(b) by 0 days.

(21) Appl. No.: 17/087,386

(22) Filed: Nov. 2, 2020

(65) Prior Publication Data

US 2022/0290158 A1 Sep. 15, 2022

Related U.S. Application Data

(60) Provisional application No. 62/929,335, filed on Nov. 1, 2019.

(51) Int. Cl.
*C12N 15/11* (2006.01)
*C12N 15/113* (2010.01)

(52) U.S. Cl.
CPC ...... *C12N 15/1138* (2013.01); *C12N 2310/11* (2013.01); *C12N 2310/14* (2013.01); *C12N 2310/531* (2013.01)

(58) Field of Classification Search
CPC ............ C12N 15/1138; C12N 2310/11; C12N 2310/14; C12N 2310/531
See application file for complete search history.

(56) References Cited

U.S. PATENT DOCUMENTS

2010/0135990 A1* 6/2010 Ichim ............... G01N 33/57426
435/375

OTHER PUBLICATIONS

Iwasaki et al, Basic fibroblast growth factor (bFGF) and vascular endothelial growth factor (VEGF) levels, as prognostic indicators in NSCLC, European Journal of Cardio-thoracic Surgery, 2004, 25: 443-448 (Year: 2004).*
Li et al, The orphan nuclear receptor EAR2 is overexpressed in colorectal cancer and it regulates survivability of colon cancer cells, Cancer Letters, 2011, 309: 137-144 (Year: 2011).*

* cited by examiner

*Primary Examiner* — Ekaterina Poliakova-Georgantas
(74) *Attorney, Agent, or Firm* — Marc Baumgartner; Baumgartner Patent Law

(57) ABSTRACT

Disclosed are means, methods and compositions of matter useful for suppressing pathological production of new blood vessels in conditions such as cancer and wet macular degeneration. In one embodiment the invention provides silencing of NR2F6 using nucleic acid based approaches such as RNA interference, antisense oligonucleotides, or DICER. In another embodiment, the invention teaches the administration of small molecule NR2F6 inhibitors as means of selectively inhibiting pathological but not healthy angiogenesis.

2 Claims, 1 Drawing Sheet

Specification includes a Sequence Listing.

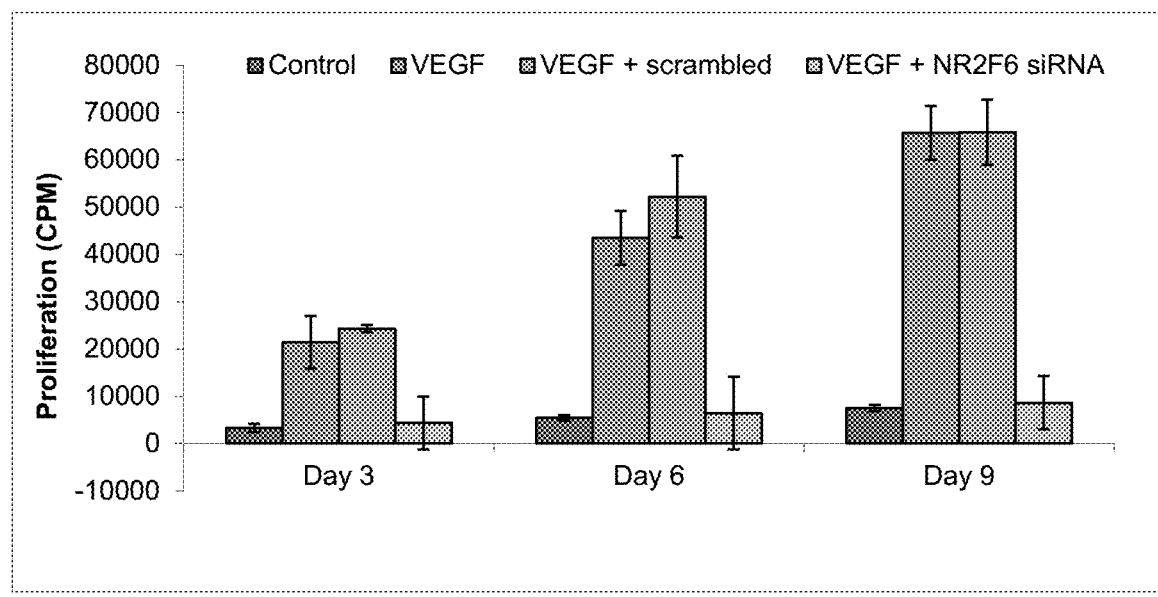

SUPPRESSION OF PATHOLOGICAL ANGIOGENESIS BY INHIBITION OF NR2F6

CROSS-REFERENCE TO RELATED APPLICATIONS

This application claims priority to U.S. Provisional Application 62/929,335, filed Nov.1, 2019, and entitled SUPPRESSION OF PATHOLOGICAL ANGIOGENESIS BY INHIBITION OF NR2F6 the contents of which are incorporated herein by reference.

SEQUENCE LISTING

The instant application contains a Sequence Listing which has been submitted electronically in ASCII format and is hereby incorporated by reference in its entirety. Said ASCII copy, created on Jul. 20, 2021, is named RegenSuppAngioNR2F6-NP1_SL.txt and is 1,245 bytes in size.

FIELD OF THE INVENTION

The invention pertains to the field of cellular biology, more importantly to the field of suppression of new blood vessels, more specifically the invention pertains to suppressing production of pathological new blood vessels using means and methods of suppressing NR2F6.

BACKGROUND OF THE INVENTION

The concept of treating cancer by blocking new blood vessel formation, angiogenesis, was pioneered by Judah Folkman who provided convincing arguments that it is not necessary to actively kill the tumor mass, but by suppressing its ability to grow through cutting off blood supply, malignant tumors may be converted into benign masses that eventually regress [1, 2]. Unfortunately, despite discovery of angiostatin, and endostatin, naturally derived inhibitors of angiogenesis, neither of these approaches translated into successful therapies[1]. Nevertheless, the concept of targeting new blood vessel formation led to thousands of publications describing various antiangiogenic agents, of which several eventually proceeded through clinical trials and regulatory approval. Broadly anti-angiogenic agents approved by regulators can be classified into antibodies, such as Bevacizumab (Avastin) which binds VEGF [3], and Ramucirumab (Cyramza) [4], which binds VEGF-R2, as well as small molecules which bind multiple receptor kinases associated with angiogenesis such as Sunitinib [5-7], Cabozantinib [8-11], Pazopanib [12-14], and Regorafenib [15-17].

These approaches have augmented the standard of care for various tumor types and have achieved some level of progress. Unfortunately, the concept of blocking angiogenesis of cancer was not as simple as originally envisioned. One of the major hurdles in blocking angiogenesis was that even though de novo blood vessels are derived from non-malignant cells, the malignant cells appear to possess ability to induce mutations in the new blood vessels. One example of the heterogeneity of tumor endothelial cells compared to endothelial cells from low and high metastatic tumors by Ohga et al [18]. The investigators extracted two types of tumor endothelial cells (TEM) from high-metastatic (HM) and low-metastatic (LM) tumors and compared their characteristics. HM tumor-derived TECs (HM-TECs) showed higher proliferative activity and invasive activity than LM tumor-derived TECs (LM-TECs). Moreover, the mRNA expression levels of pro-angiogenic genes, such as vascular endothelial growth factor (VEGF) receptors 1 and 2, VEGF, and hypoxia-inducible factor-1α, were higher in HM-TECs than in LM-TECs. The tumor blood vessels themselves and the surrounding area in HM tumors were exposed to hypoxia. Furthermore, HM-TECs showed higher mRNA expression levels of the stemness-related gene stem cell antigen and the mesenchymal marker CD90 compared with LM-TECs. HM-TECs were spheroid, with a smoother surface and higher circularity in the stem cell spheroid assay. HM-TECs differentiated into osteogenic cells, expressing activated alkaline phosphatase in an osteogenic medium at a higher rate than either LM-TECs or normal ECs. Furthermore, HM-TECs contained more aneuploid cells than LM-TECs. The investigators concluded that the results indicate that TECs from HM tumors have a more pro-angiogenic phenotype than those from LM tumors. It appears that the aggressiveness of the tumor not only can alter endothelial cell function but also drug resistance ability. In another study, Akiyama et al. [19]compared murine TECs and normal ECs. It was found that TECs were more resistant to paclitaxel with the up-regulation of multidrug resistance (MDR) 1 mRNA, which encodes the P-glycoprotein, compared with normal ECs. Normal human microvascular ECs were cultured in tumor-conditioned medium (CM) and became more resistant to paclitaxel through MDR1 mRNA up-regulation and nuclear translocation of Y-box-binding protein 1, which is an MDR1 transcription factor. Vascular endothelial growth factor (VEGF) receptor 2 (VEGFR2) and Akt were activated in human microvascular ECs by tumor CM. The investigators observed that tumor CM contained a significantly high level of VEGF. A VEGFR kinase inhibitor, Ki8751, and a phosphatidylinositol 3-kinase-Akt inhibitor, LY294002, blocked tumor CM-induced MDR1 up-regulation. MDR1 up-regulation, via the VEGF-VEGFR pathway in the tumor microenvironment, is one of the mechanisms of drug resistance acquired by TECs. It was observed that VEGF secreted from tumors up-regulated MDR1 through the activation of VEGFR2 and Akt. This process is a novel mechanism of the acquisition of drug resistance by TECs in the tumor microenvironment. Yet another study demonstrated that tumors can induce a "dedifferentiation" of tumor endothelium. Specifically, compared with NECs, stem cell markers such as Sca-1, CD90, and multidrug resistance 1 are upregulated in TECs, suggesting that stem-like cells exist in tumor blood vessels. TECs and NECs were isolated from melanoma-xenografted nude mice and normal dermis, respectively. The stem cell marker aldehyde dehydrogenase (ALDH) mRNA expression and activity were higher in TECs than those in NECs. Next, ALDHhigh/low TECs were isolated by fluorescence-activated cell sorting to compare their characteristics. Compared with ALDHlow TECs, ALDHhigh TECs formed more tubes on Matrigel-coated plates and sustained the tubular networks longer. Furthermore, VEGFR2 expression was higher in ALDHhigh TECs than that in ALDHlow TECs. In addition, ALDH was expressed in the tumor blood vessels of in vivo mouse models of melanoma and oral carcinoma, but not in normal blood vessels. These findings indicate that ALDHhigh TECs exhibit an angiogenic phenotype. Stem-like TECs may have an essential role in tumor angiogenesis [20].

What is it that causes the tumor to evoke changes in the endothelium? As suggested above, there is some support for growth factor mediated alterations, additionally, horizontal gene transfer may also play a role [21-29]. Although the field of horizontal gene transfer has historically been controversial one of the strongest evidences supporting this concept is the phenomena of donor-derived relapse in leukemic patients. In these situations patients with leukemia who relapse after bone marrow transplant have the relapsing cells originate from donor cells that transformed into malignant cells [30, 31]. Another issue that affected efficacy of anti-angiogenesis therapies is that in some tumors, the tumor cells themselves transdifferentiate into endothelial-like cells, termed tumor vascular channels, which possess ability to mutate around either antibody or kinase inhibitor drugs [32-37].

The previously mentioned means by which tumor endothelial cells can protect themselves against anti-angiogenic agents has resulted in relatively low clinical efficacy of these drugs. To understand the general lack of efficacy in the initial registration trial[2], median progression free survival (PFS) of ovarian cancer patients who received bevacizumab plus chemotherapy was 6.8 months (95 percent CI: 5.6, 7.8) compared with 3.4 months (95 percent CI: 2.1, 3.8) for those who received chemotherapy alone. There was no statistically significant difference in overall survival (OS) for patients treated with bevacizumab plus chemotherapy compared with chemotherapy alone (median OS: 16.6 months versus 13.3 months; HR 0.89; 95 percent CI: 0.69, 1.14). Subset analysis led to identification that the group of patients that received paclitaxel with the antibody had the largest improvement, resulting in a 5.7-month improvement in median PFS (9.6 months versus 3.9 months; HR 0.47; 95 percent CI: 0.31, 0.72), an improvement in the objective response rate (53 percent versus 30 percent), and a 9.2-month improvement in median OS (22.4 months versus 13.2 months, HR 0.64; 95 percent CI: 0.41, 1.01)[3]. Multiple other trials where conducted for different indications using bevacizumab, unfortunately, progression free survival and overall survival was not increase more than a year in any of the studies [38-42], and neither in studies with small molecule kinase inhibitors [43-48].

This clinical translation, although highly beneficial in some patients, overall the effect was mediocre, highlights the disparity between animal studies, in which some studies complete regression was observed in established tumors [49, 50], whereas in clinical trials, relatively minimal effect compared to animal studies was observed [51]. One lesson from these studies is that the large heterogeneity of the patient and of the tumors, which calls for large patient populations in order to achieve an overall survival advantage. Innovations in pharmacogenomics and personalized medicine will help identify specific patients and tumors that are likely to respond. Unfortunately, at present, patients with metastatic disease have limited options and a statistically significant extension of survival does equate to large market demand, as seen by the overall sale of angiogenesis inhibitors for cancer being over 20 billion annually.

SUMMARY OF THE INVENTION

Preferred embodiments herein are directed to method of suppressing pathological angiogenesis comprising the step of inhibiting NR2F6 transcription, and/or translation, and/or function.

Preferred teachings herein include embodiments wherein said pathological angiogenesis is induced by vascular endothelial growth factor (VEGF).

Preferred teachings herein include embodiments wherein said pathological angiogenesis is associated with neoplastic tissue.

Preferred teachings herein include embodiments wherein said pathological angiogenesis is associated with macular degeneration.

Preferred teachings herein include embodiments wherein inhibition of NR2F6 is caused by a method chosen from a group comprising of: a) short interfering RNA; b) short hairpin RNA; c) antisense oligonucleotides; d) ribozyme mRNA; and e) decoy oligonucleotides.

Preferred teachings herein include embodiments wherein said short interfering

RNA comprises of a sense sequence of 5'-GAT CCG CAT TAC GGT GTC TTC ACC TTC AAG AGA GGT GAA GAC ACC GTA ATG CTT TTT TCT AGA G-3' (SEQ ID NO: 1) or a sense sequence of 5'-GAT CCG CCT CTG GAC ACG TAA CCT ATT CAA GAG ATA GGT TAC GTG TCC AGA GGT TTT TTC TAG AG-3' (SEQ ID NO: 3)

Preferred teachings herein include embodiments wherein said siRNA sequence is administered in the form of a hairpin loop.

Preferred teachings herein include embodiments wherein said RNA sequence is administered at a concentration sufficient to induce the process of RNA interference.

Preferred teachings herein include embodiments wherein said induction of RNA interference is associated with activation of DICER.

Preferred teachings herein include embodiments wherein said inhibition of function of NR2F6 is induced by administration of a small molecule.

Preferred teachings herein include methods of inhibiting cancer associated angiogenesis comprising the step of inhibiting NR2F6 transcription, and/or translation, and/or function.

Preferred teachings herein include embodiments wherein said pathological angiogenesis is induced by vascular endothelial growth factor (VEGF).

Preferred teachings herein include embodiments wherein said pathological angiogenesis is associated with neoplastic tissue.

Preferred teachings herein include embodiments wherein said pathological angiogenesis is associated with macular degeneration.

Preferred teachings herein include embodiments wherein inhibition of NR2F6 is caused by a method chosen from a group comprising of: a) short interfering RNA; b) short hairpin RNA; c) antisense oligonucleotides; d) ribozyme mRNA; and e) decoy oligonucleotides.

Preferred teachings herein include embodiments wherein said short interfering

RNA comprises of a sense sequence of 5'-GAT CCG CAT TAC GGT GTC TTC ACC TTC AAG AGA GGT GAA GAC ACC GTA ATG CTT TTT TCT AGA G-3' (SEQ ID NO: 1) or a sense sequence of 5'-GAT CCG CCT CTG GAC ACG TAA CCT ATT CAA GAG ATA GGT TAC GTG TCC AGA GGT TTT TTC TAG AG-3' (SEQ ID NO: 3)

Preferred teachings herein include embodiments wherein said siRNA sequence is administered in the form of a hairpin loop.

Preferred teachings herein include embodiments wherein said RNA sequence is administered at a concentration sufficient to induce the process of RNA interference.

Preferred teachings herein include embodiments wherein said induction of RNA interference is associated with activation of DICER.

Preferred teachings herein include embodiments wherein said inhibition of function of NR2F6 is induced by administration of a small molecule.

BRIEF DESCRIPTION OF THE DRAWINGS

FIG. 1 is a bar graph showing selective suppression of VEGF induced angiogenesis by NR2F6 inhibition.

DETAILED DESCRIPTION OF THE INVENTION

The invention relates to the previously unknown finding that inhibition of NR2F6 is associated with suppression pathological angiogenesis.

The term "NR2F6" as used herein refers to nuclear receptor subfamily2, group F, member 6 and is also referred to as v-erbA-related gene or ear-2

The term "oligonucleotide" is intended to include unmodified DNA or RNA or modified DNA or RNA. For example, the nucleic acid molecules or polynucleotides of the disclosure can be composed of single- and double stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

The term "animal" as used herein includes all members of the animal kingdom, preferably mammal. The term "mammal" as used herein is meant to encompass, without limitation, humans, domestic animals such as dogs, cats, horses, cattle, swine, sheep, goats, and the like, as well as wild animals. In an embodiment, the mammal is human.

The term "interfering RNA" or "RN Ai" or "interfering RNA sequence" refers to double-stranded RNA (i.e., duplex RNA) that targets (i.e., silences, reduces, or inhibits) expression of a target gene (i.e., by mediating the degradation of mRNAs which are complementary to the sequence of the interfering RNA) when the interfering RNA is in the same cell as the target gene, Interfering RNA thus refers to the double stranded RNA formed by two complementary strands or by a single, self-complementary strand. Interfering RNA typically has substantial or complete identity to the target gene. The sequence of the interfering RNA can correspond to the full length target gene, or a subsequence thereof. Interfering RNA includes small-interfering RNA" or "siRNA," i.e., interfering RNA of about 1.5-60, 15-50, 15-50, or 15-40 (duplex) nucleotides in length, more typically about, 15-30, 15-25 or 19-25 (duplex) nucleotides in length, and is preferably about 20-24 or about 21-22 or 21-23 (duplex) nucleotides in length (e.g., each complementary sequence of the double stranded siRNA is 15-60, 15-50, 15-50, 15-40, 15-30, 15-25 or 19-25 nucleotides in length, preferably about 20-24 or about 21-22 or 21-23 nucleotides in length, and the double stranded siRNA is about 15-60, 15-50, 15-50, 15-40, 15-30, 15-25 or 19-25 preferably about 20-24 or about 21-22 or 21-23 base pairs in length). siRNA duplexes may comprise 3' overhangs of about 1 to about 4 nucleotides, preferably of about 2 to about 3 nucleotides and 5' phosphate termini. The siRNA can be chemically synthesized or maybe encoded by a plasmid (e.g., transcribed as sequences that automatically fold into duplexes with hairpin loops). siRNA can also be generated by cleavage of longer dsRNA. (e.g., dsRNA greater than about 25 nucleotides in length) with the E. coli RNase III or Dicer. These enzymes process the dsRNA into biologically active siRNA (see, e.g., Yang et al., *PNAS USA* 99: 9942-7 (2002); Calegari et al., *PNAS USA* 99: 14236 (2002); Byrom et al., *Ambion Tech-Notes* 10(1): 4-6 (2003); Kawasaki et al., *Nucleic Acids Res.* 31: 981-7 (2003); Knight and Bass, *Science* 293: 2269-71 (2001); and Robertson et at, *J. Biol. Chem.* 243: 82 (1968)). Preferably, dsRNA are at least 50 nucleotides to about 100, 200, 300, 400 or 500 nucleotides in length. A dsRNA may be as long as 1000, 1500, 2000, 5000 nucleotides in length, or longer. The dsRNA can encode for an entire gene transcript or a partial gene transcript.

The term "siRNA" refers to a short inhibitory RNA that can be used to silence gene expression of a specific gene. The siRNA can be a short RNA hairpin (e.g. shRNA) that activates a cellular degradation pathway directed at mRNAs corresponding to the siRNA. Methods of designing specific siRNA molecules or shRNA molecules and administering them are known to a person skilled in the art. It is known in the art that efficient silencing is obtained with siRNA duplex complexes paired to have a two nucleotide 3' overhang. Adding two thymidine nucleotides is thought to add nuclease resistance. A person skilled in the art will recognize that other nucleotides can also be added.

The term "antisense nucleic acid" as used herein means a nucleotide sequence that is complementary to its target e.g. a NR2F6 transcription product. The nucleic acid can comprise DNA, RNA or a chemical analog, that binds to the messenger RNA produced by the target gene. Binding of the antisense nucleic acid prevents translation and thereby inhibits or reduces target protein expression. Antisense nucleic acid molecules may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

As used in this context, to "treat" means to ameliorate at least one symptom of the disorder. In some embodiments, a treatment can result in a reduction in tumor size or number, or a reduction in tumor growth or growth rate.

One embodiment of the invention is a short-interfering ribonucleic acid (siRNA) molecule effective at silencing NR2F6 expression or substantially inhibiting NR2F6 expression. In one embodiment of the invention the oligonucleotide backbone is chemically modified to increase the deliverability of the interfering ribonucleic acid molecule. In another embodiment these chemical modifications act to neutralize the negative charge of the interfering ribonucleic acid molecule. One embodiment of the invention consists of a pharmaceutical composition comprising an siRNA oligonucleotide that induces RNA interference against NR2F6. It is known to one of skill in the art that siRNAs induce a sequence-specific reduction in expression of a gene by the process of RNAi, as previously mentioned. Thus, siRNA is the intermediate effector molecule of the RNAi process that is normally induced by double stranded viral infections, with the longer double stranded RNA being cleaved by naturally occurring enzymes such as DICER. Some nucleic acid molecules or constructs provided herein include double stranded RNA molecules comprising 16-30, e.g., 16, 17, 18, 19, 20, 21, 22, 23, 24, 25, 26, 27, 28, 29, or 30 nucleotides in each strand, wherein one of the strands is substantially identical, for example at least 85% (or more, as for example, 90%, 95%, or 100%) identical, e.g., having 3, 2, 1, or 0 mismatched nucleotide(s), to a target region in the mRNA of NR2F6 and the other strand is identical or substantially identical to the first strand. However, it will be appreciated that the dsRNA molecules may have any number of nucleotides in each strand which allows them to reduce the level of NR2F6 protein, or the level of a nucleic acid encoding NR2F6 . The dsRNA molecules provided herein can be chemically synthesized, or can be transcribed in vitro from a DNA template, or in vivo from, e.g., shRNA, which is mentioned below. The dsRNA molecules can be designed using any method known in the art.

In one embodiment, nucleic acids provided herein can include both unmodified siRNAs and modified siRNAs as known in the art. For example, in some embodiments, siRNA derivatives can include siRNA having two complementary strands of nucleic acid, such that the two strands are crosslinked. For a specific example, a 3' OH terminus of one of the strands can be modified, or the two strands can be crosslinked and modified at the 3' OH terminus. The siRNA derivative can contain a single crosslink (one example of a useful crosslink is a psoralen crosslink). In some embodiments, the siRNA derivative has at its 3' terminus a biotin molecule (for example, a photocleavable molecule such as biotin), a peptide (as an example an HIV Tat peptide), a nanoparticle, a peptidomimetic, organic compounds, or dendrimer. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acids described within the practice of the current invention can include nucleic acids that are unconjugated or can be conjugated to another moiety, such as a nanoparticle, to enhance a desired property of the pharmaceutical composition. Properties useful in the development of a therapeutic agent include: a) absorption; b) efficacy; c) bioavailability; and d) half life in blood or in vivo. RNAi is believed to progress via at least one single stranded RNA intermediate, the skilled artisan will appreciate that single stranded-siRNAs (e.g., the antisense strand of a ds-siRNA) can also be designed as described herein and utilized according to the claimed methodologies.

In one embodiment the pharmaceutical composition comprises a nucleic acid-lipid particle that contains an siRNA oligonucleotide that induces RNA interference against NR2F6. In some aspects the lipid portion of the particle comprises a cationic lipid and a non-cationic lipid. In some aspects the nucleic acid-lipid particle further comprises a conjugated lipid that prevents aggregation of the particles and/or a sterol (e.g., cholesterol).

For practice of the invention, methods for expressing siRNA duplexes within cells from recombinant DNA constructs to allow longer-term target gene suppression in cells are known in the art, including mammalian Pol III promoter systems (e.g., H1 or U6/snRNA promoter systems) capable of expressing functional double-stranded siRNAs. Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by an H1 or U6 snRNA promoter can be expressed in cells, and can inhibit target gene expression. Constructs containing siRNA sequence(s) under the control of a T7 promoter also make functional siRNAs when co-transfected into the cells with a vector expressing T7 RNA polymerase. A single construct may contain multiple sequences coding for siRNAs, such as multiple regions of the NR2F6 gene, such as a nucleic acid encoding the NR2F6 mRNA, and can be driven, for example, by separate Pol III promoter sites. In some situations it will be preferable to induce expression of the hairpin siRNA or shRNAs in a tissue specific manner in order to activate the shRNA transcription that would subsequently silence NR2F6 expression. Tissue specificity may be obtained by the use of regulatory sequences of DNA that are activated only in the desired tissue. Regulatory sequences include promoters, enhancers and other expression control elements such as polyadenylation signals. Regulatory sequences include those which direct constitutive expression of a nucleotide sequence in many types of host cell and those which direct expression of the nucleotide sequence only in certain host cells. Tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, promoters as follows may be used to target gene expression in other tissues. Examples of more tissue specific promoters include in (a) to target the pancreas promoters for the following may be used: insulin, elastin, amylase, pdr-I, pdx-I, glucokinase; (b) to target the liver promoters for the following may be used: albumin PEPCK, HBV enhancer, a fetoprotein, apolipoprotein C, .alpha.-I antitrypsin, vitellogenin, NF-AB, Transthyretin; (c) to target the skeletal muscle promoters for the following may be used: myosin H chain, muscle creatine kinase, dystrophin, calpain p94, skeletal .alpha.-actin, fast troponin 1; (d) to target the skin promoters for the following may be used: keratin K6, keratin KI; (e) lung: CFTR, human cytokeratin IS (K 18), pulmonary surfactant proteins A, B and C, CC-10, Pi; (0 smooth muscle: sm22 .alpha., SM-.alpha.-actin; (g) to target the endothelium promoters for the following may be used: endothelin-I, E-selectin, von Willebrand factor, TIE, KDR/flk-I; (h) to target melanocytes the tyrosinase promoter may be used; (i) to target the mammary gland promoters for the following may be used: MMTV, and whey acidic protein (WAP).

Yet another embodiment of the invention consists of a pharmaceutical composition comprising an oligonucleotide that induces RNA interference against NR2F6 combined with a delivery agent such as a liposome. For more targeted delivery immunoliposomes, or liposomes containing an agent inducing selective binding to neoplastic cells may be used.

The present invention further provides pharmaceutical compositions comprising the nucleic acid-lipid particles described herein and a pharmaceutically acceptable carrier.

Another embodiment of the invention consists of a pharmaceutical composition comprising an oligonucleotide that induces RNA interference against NR2F6 combined with an additional chemotherapeutic agent.

Yet another embodiment of the invention consists of a pharmaceutical composition comprising an oligonucleotide that induces RNA interference against NR2F6 combined with an additional agent used to induce differentiation of endothelial cells associated with cancer.

One embodiment of the invention is a short-interfering ribonucleic acid (siRNA) molecule effective at silencing NR2F6 expression that has been cloned into an appropriate expression vector giving rise to an shRNA vector.

In certain embodiment shRNA olignucleotides are cloned into an appropriate mammalian expression vectors, examples of appropriate vectors include but are not limited to lentiviral, retroviral or adenoviral vector.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

For the purpose of the invention, suppression of NR2F6 is performed in endothelial cells associated with pathology such as in cancer or wet macular degeneration. RNA interference "RNAi" is mediated by double stranded RNA (dsRNA) molecules that have sequence-specific homology to their "target" nucleic acid sequences (Caplen, N. J., et al. (2001) Proc. Natl. Acad. Sci. USA 98:9742-9747). In certain embodiments of the present invention, the mediators are 5-25 nucleotide "small interfering" RNA duplexes (siRNAs). The siRNAs are derived from the processing of dsRNA by an RNase enzyme known as Dicer (Bernstein, E., et al. (2001) Nature 409:363-366). siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al. (2001) Nature 409:363-366; Boutla, A., et al. (2001) Curr. Biol. 11:1776-1780). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner et al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Komberg and Baker, DNA Replication, 2nd Ed. (Freeman, San Francisco, 1992) as well as their analogs.

As used herein, the term "cancer" refers to any malignant tumor, particularly arising in the lung, kidney, or thyroid. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. As noted above, the invention specifically permits differential diagnosis of lung, kidney, and thyroid tumors.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In another preferred embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs). It is currently not known whether RNAa is conserved in other organisms.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound.

The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines (Hammond et al., (1991) Nat. Rev. Genet., 2, 110-119; Matzke et al., (2001) Curr. Opin. Genet. Dev., 11, 221-227; Sharp, (2001) Genes Dev., 15, 485-490). When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

In one embodiment the invention teaches the combined use of NR2F6 inhibition with other agents which potential killing of endothelial cells associated with pathological angiogenesis. On possible combination agent is rapamycin. In one series of experiments tumor bearing animals where treated with rapamycin and the results showed that CD34(+) blood vessels and LYVE-1(+) lymphatic vessels decreased in the peritumor and intratumor region in rapamycin-treated tumors. Expression of p-4EBP1 and p-S6K1 proteins was downregulated. Expression of both proteins and mRNAs of VEGF-A/VEGFR-2 and VEGF-C/VEGFR-3 was downregulated [52].

EXAMPLE 1: SELECTIVE SUPPRESSION OF VEGF INDUCED ANGIOGENESIS BY NR2F6 INHIBITION

HUVEC cells where purchased from AllCells and grown according to the manufacturers instructions. Pathological-like angiogenesis was triggered by 3, 6, and 9 day culture with VEGF. Inhibition of NR2F6 was accomplished by transfection of cells with siRNA targeting NR2F6 using lipofectamine. Sequence for the siRNA was sense sequence of 5'-GAT CCG CAT TAC GGT GTC TTC ACC TTC AAG AGA GGT GAA GAC ACC GTA ATG CTT TTT TCT AGA G-3'. (SEQ ID NO: 1) Scrambled siRNA was sense sequence of 5'-GTT CGG CTT TAA GGT GTC TTC ACC TTC AGG AAA GTT GTA GTC TCC GTT TTG CGT GTT TAT AAA G-3'. (SEQ ID NO: 2) siRNA was also incubated with cells for 3, 6, and 9 days. Proliferation was assessed by tritiated thymidine incorporation and quantified as counts per minute. The results are shown in the bar graph of FIG. 1.

REFERENCES

1. Cao, Y., et al., *Forty-year journey of angiogenesis translational research*. Sci Transl Med, 2011. 3(114): p. 114rv3.
2. Abdollahi, A. and J. Folkman, *Evading tumor evasion: current concepts and perspectives of anti-angiogenic cancer therapy*. Drug Resist Updat, 2010. 13(1-2): p. 16-28.
3. Chen, H. X., R. E. Gore-Langton, and B. D. Cheson, *Clinical trials referral resource: Current clinical trials of the anti-VEGF monoclonal antibody bevacizumab*. Oncology (Williston Park), 2001. 15(8): p. 1017, 1020, 1023-6.
4. Krupitskaya, Y. and H. A. Wakelee, *Ramucirumab, a fully human mAb to the transmembrane signaling tyrosine kinase VEGFR-2 for the potential treatment of cancer*. Curr Opin Investig Drugs, 2009. 10(6): p. 597-605.
5. Abrams, T. J., et al., *SU11248 inhibits KIT and platelet-derived growth factor receptor beta in preclinical models of human small cell lung cancer*. Mol Cancer Ther, 2003. 2(5): p. 471-8.
6. Carlisle, B., et al., *Benefit, Risk, and Outcomes in Drug Development: A Systematic Review of Sunitinib*. J Natl Cancer Inst, 2016. 108(1).
7. Izzedine, H., et al., *Sunitinib malate*. Cancer Chemother Pharmacol, 2007. 60(3): p. 357-64.
8. Viola, D., V. Cappagli, and R. Elisei, *Cabozantinib (XL184) for the treatment of locally advanced or metastatic progressive medullary thyroid cancer*. Future Oncol, 2013. 9(8): p. 1083-92.
9. Roy, S., et al., *A novel multiple tyrosine-kinase targeted agent to explore the future perspectives of anti-angiogenic therapy for the treatment of multiple solid tumors: cabozantinib*. Anticancer Agents Med Chem, 2015. 15(1): p. 37-47.
10. Tannir, N. M., G. Schwab, and V. Grunwald, *Cabozantinib: an Active Novel Multikinase Inhibitor in Renal Cell Carcinoma*. Curr Oncol Rep, 2017. 19(2): p. 14.
11. Yakes, F. M., et al., *Cabozantinib (XL184), a novel MET and VEGFR2 inhibitor, simultaneously suppresses metastasis, angiogenesis, and tumor growth*. Mol Cancer Ther, 2011. 10(12): p. 2298-308.
12. Gril, B., et al., *The B-Raf status of tumor cells may be a significant determinant of both antitumor and anti-angiogenic effects of pazopanib in xenograft tumor models*. PLoS One, 2011. 6(10): p. e 25625.
13. van Geel, R. M., J. H. Beijnen, and J. H. Schellens, *Concise drug review: pazopanib and axitinib*. Oncologist, 2012. 17(8): p. 1081-9.
14. Ferrero, S., et al., *Pharmacokinetic drug evaluation of pazopanib for the treatment of uterine leiomyosarcomas*. Expert Opin Drug Metab Toxicol, 2017. 13(8): p. 881-889.
15. Gaumann, A. K., et al., *Receptor tyrosine kinase inhibitors: Are they real tumor killers?* Int J Cancer, 2016. 138(3): p. 540-54.
16. Miura, K., et al., *The preclinical development of regorafenib for the treatment of colorectal cancer*. Expert Opin Drug Discov, 2014. 9(9): p. 1087-101.
17. Rimassa, L., et al., *Regorafenib for the treatment of unresectable hepatocellular carcinoma*. Expert Rev Anticancer Ther, 2017. 17(7): p. 567-576.
18. Ohga, N., et al., *Heterogeneity of tumor endothelial cells: comparison between tumor endothelial cells isolated from high- and low-metastatic tumors*. Am J Pathol, 2012. 180(3): p. 1294-307.
19. Akiyama, K., et al., *Tumor endothelial cells acquire drug resistance by MDR1 up-regulation via VEGF signaling in tumor microenvironment*. Am J Pathol, 2012. 180(3): p. 1283-93.
20. Ohmura-Kakutani, H., et al., *Identification of tumor endothelial cells with high aldehyde dehydrogenase activity and a highly angiogenic phenotype*. PLoS One, 2014. 9(12): p. e 113910.
21. Sruthi, T. V., et al., *Horizontal transfer of miR-23 a from hypoxic tumor cell colonies can induce angiogenesis*. J Cell Physiol, 2017.
22. Kosaka, N., et al., *Neutral sphingomyelinase 2 (nSMase2)-dependent exosomal transfer of angiogenic microRNAs regulate cancer cell metastasis*. J Biol Chem, 2013. 288(15): p. 10849-59.
23. Zhang, Y., et al., *Tumacrophage: macrophages transformed into tumor stem-like cells by virulent genetic material from tumor cells*. Oncotarget, 2017. 8(47): p. 82326-82343.
24. Abdouh, M., et al., *Exosomes isolated from cancer patients' sera transfer malignant traits and confer the same phenotype of primary tumors to oncosuppressor-mutated cells*. J Exp Clin Cancer Res, 2017. 36(1): p. 113.
25. Semina, S. E., et al., *Horizontal Transfer of Tamoxifen Resistance in MCF-7 Cell Derivates: Proteome Study*. Cancer Invest, 2017. 35(8): p. 506- 518.
26. Cal, J., et al., *Functional transferred DNA within extracellular vesicles*. Exp Cell Res, 2016. 349(1): p. 179-183.
27. Hamam, D., et al., *Transfer of malignant trait to BRCA1 deficient human fibroblasts following exposure to serum of cancer patients*. J Exp Clin Cancer Res, 2016. 35: p. 80.
28. Berridge, M. V., L. Dong, and J. Neuzil, *Mitochondrial DNA in Tumor Initiation, Progression, and Metastasis: Role of Horizontal mtDNA Transfer*. Cancer Res, 2015. 75(16): p. 3203-8.
29. Chen, W. X., et al., *Exosomes from drug-resistant breast cancer cells transmit chemoresistance by a horizontal transfer of microRNAs*. PLoS One, 2014. 9(4): p. e95240.
30. Zhu, X., et al., *BCR-ABL1-positive microvesicles transform normal hematopoietic transplants through genomic instability: implications for donor cell leukemia*. Leukemia, 2014. 28(8): p. 1666-75.

31. Stein, J., et al., *Origin of leukemic relapse after bone marrow transplantation: comparison of cytogenetic and molecular analyses.* Blood, 1989. 73(7): p. 2033-40.
32. Angara, K., T. F. Bonin, and A. S. Arbab, *Vascular Mimicry: A Novel Neovascularization Mechanism Driving Anti-Angiogenic Therapy (AAT) Resistance in Glioblastoma.* Transl Oncol, 2017. 10(4): p. 650-660.
33. Sood, A. K., et al., *The clinical significance of tumor cell-lined vasculature in ovarian carcinoma: implications for anti-vasculogenic therapy.* Cancer Biol Ther, 2002. 1(6): p. 661-4.
34. Mahase, S., et al., *Hypoxia-Mediated Mechanisms Associated with Antiangiogenic Treatment Resistance in Glioblastomas.* Am J Pathol, 2017. 187(5): p. 940-953.
35. Pinto, M. P., et al., *Escaping Antiangiogenic Therapy: Strategies Employed by Cancer Cells.* Int J Mol Sci, 2016. 17(9).
36. Schnegg, C. I., et al., *Induction of Vasculogenic Mimicry Overrides VEGF-A Silencing and Enriches Stem-like Cancer Cells in Melanoma.* Cancer Res, 2015. 75(8): p. 1682-90.
37. Soda, Y., et al., *Transdifferentiation of glioblastoma cells into vascular endothelial cells.* Proc Natl Acad Sci U S A, 2011. 108(11): p. 4274-80.
38. Li, Q., et al., *Angiogenesis inhibitors for the treatment of small cell lung cancer (SCLC): A meta-analysis of 7 randomized controlled trials.* Medicine (Baltimore), 2017. 96(13): p. e6412.
39. Lombardi, G., et al., *Effectiveness of antiangiogenic drugs in glioblastoma patients: A systematic review and meta-analysis of randomized clinical trials.* Crit Rev Oncol Hematol, 2017. 111: p. 94-102.
40. Roviello, G., et al., *The role of bevacizumab in solid tumours: A literature based meta-analysis of randomised trials.* Eur J Cancer, 2017. 75: p. 245-258.
41. Shih, T. and C. Lindley, *Bevacizumab: an angiogenesis inhibitor for the treatment of solid malignancies.* Clin Ther, 2006. 28(11): p. 1779-802.
42. Chase, J. L., *Clinical use of anti-vascular endothelial growth factor monoclonal antibodies in metastatic colorectal cancer.* Pharmacotherapy, 2008. 28(11 Pt 2): p. 23S-30S.
43. Yu, J., et al., *Efficacy and safety of angiogenesis inhibitors in advanced gastric cancer: a systematic review and meta-analysis.* J Hematol Oncol, 2016. 9(1): p. 111.
44. Ciliberto, D., et al., *A systematic review and meta-analysis of randomized trials on the role of targeted therapy in the management of advanced gastric cancer: Evidence does not translate?* Cancer Biol Ther, 2015. 16(8): p. 1148-59.
45. Welsh, S. J. and K. Fife, *Pazopanib for the treatment of renal cell carcinoma.* Future Oncol, 2015. 11(8): p. 1169-79.
46. Khan, K., D. Cunningham, and I. Chau, *Targeting Angiogenic Pathways in Colorectal Cancer: Complexities, Challenges and Future Directions.* Curr Drug Targets, 2017. 18(1): p. 56-71.
47. Iacovelli, R., et al., *Inhibition of the VEGF/VEGFR pathway improves survival in advanced kidney cancer: a systematic review and meta-analysis.* Curr Drug Targets, 2015. 16(2): p. 164-70.
48. Piperdi, B., A. Merla, and R. Perez-Soler, *Targeting angiogenesis in squamous non-small cell lung cancer.* Drugs, 2014. 74(4): p. 403-13.
49. von Baumgarten, L., et al., *Bevacizumab has differential and dose-dependent effects on glioma blood vessels and tumor cells.* Clin Cancer Res, 2011. 17(19): p. 6192-205.
50. Yuan, F., et al., *Time-dependent vascular regression and permeability changes in established human tumor xenografts induced by an anti-vascular endothelial growth factor/vascular permeability factor antibody.* Proc Natl Acad Sci U S A, 1996. 93(25): p. 14765-70.
51. Aalders, K. C., et al., *Anti-angiogenic treatment in breast cancer: Facts, successes, failures and future perspectives.* Cancer Treat Rev, 2017. 53: p. 98-110.
52. Wang, M., et al., *Rapamycin suppresses angiogenesis and lymphangiogenesis in melanoma by downregulating VEGF-A/VEGFR-2 and VEGF-C/VEGFR-3 expression.* Onco Targets Ther, 2019. 12: p. 4643-4654.

---

The invention claimed is:

1. A method of suppressing pathological angiogenesis associated with macular degeneration comprising the step of inhibiting NR2F6 transcription performed by using an oligonucleotide selected from the group consisting of a) short interfering RNA; b) short hairpin RNA; c) antisense oligonucleotide.

2. The method of claim 1, wherein said short interfering RNA comprises a sequence of 5'-GAT CCG CAT TAC GGT GTC TTC ACC TTC AAG AGA GGT GAA GAC ACC GTA ATG CTT TTT TCT AGA G-3' (SEQ ID NO: 1) or a sequence of 5'-GAT CCG CCT CTG GAC ACG TAA CCT ATT CAA GAG ATA GGT TAC GTG TCC AGA GGT TTT TTC TAG AG-3' (SEQ ID NO: 3).

* * * * *

SEQUENCE LISTING

<160> NUMBER OF SEQ ID NOS: 3

<210> SEQ ID NO 1
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gatccgcatt acggtgtctt caccttcaag agaggtgaag acaccgtaat gcttttttct      60
agag                                                                  64

<210> SEQ ID NO 2
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 2
gttcggcttt aaggtgtctt caccttcagg aaagttgtag tctccgtttt gcgtgtttat    60
aaag                                                                64

<210> SEQ ID NO 3
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatccgcctc tggacacgta acctattcaa gagataggtt acgtgtccag aggttttttc    60
tagag                                                               65
```